(12) United States Patent
Schober et al.

(10) Patent No.: US 10,006,835 B2
(45) Date of Patent: Jun. 26, 2018

(54) SENSOR DEVICE WITH MAGNET AND SENSOR ARRAY FOR TIRE INSPECTION

(71) Applicants: Bradley D. Schober, Greer, SC (US); Frank E. Gramling, Greenville, SC (US); David A. Judd, Mauldin, SC (US)

(72) Inventors: Bradley D. Schober, Greer, SC (US); Frank E. Gramling, Greenville, SC (US); David A. Judd, Mauldin, SC (US)

(73) Assignee: COMPAGNIE GENERALE DES ETABLISSEMENTS MICHELIN, Clermont-Ferrand (FR)

(*) Notice: Subject to any disclaimer, the term of this patent is extended or adjusted under 35 U.S.C. 154(b) by 191 days.

(21) Appl. No.: 15/112,718

(22) PCT Filed: Mar. 13, 2014

(86) PCT No.: PCT/US2014/026021
§ 371 (c)(1),
(2) Date: Jul. 20, 2016

(87) PCT Pub. No.: WO2015/137951
PCT Pub. Date: Sep. 17, 2015

(65) Prior Publication Data
US 2016/0349149 A1 Dec. 1, 2016

(51) Int. Cl.
*G01M 17/02* (2006.01)
*G01M 5/00* (2006.01)
(Continued)

(52) U.S. Cl.
CPC .......... *G01M 17/02* (2013.01); *G01M 5/0033* (2013.01); *G01M 5/0091* (2013.01);
(Continued)

(58) Field of Classification Search
None
See application file for complete search history.

(56) References Cited

U.S. PATENT DOCUMENTS

| 4,936,138 A * | 6/1990 | Cushman | G01M 17/025 |
| | | | 73/146 |
| 6,255,940 B1 * | 7/2001 | Phelan | B60C 23/0433 |
| | | | 152/152.1 |

(Continued)

FOREIGN PATENT DOCUMENTS

| EP | 2085253 A1 | 8/2009 |
| WO | WO 2006/067361 A1 | 6/2006 |

OTHER PUBLICATIONS

European Search report for Application No. 14885755.7 dated Sep. 28, 2017 9 pgs.
(Continued)

*Primary Examiner* — Jill Culler
(74) *Attorney, Agent, or Firm* — Dority & Manning, P.A.

(57) ABSTRACT

A sensor device is provided for use in tire inspection along a bead portion of the tire. The sensor device includes a magnet array configured to provide the desired fields of magnet flux for a sensor array, which is used to detect damage to reinforcements of a body ply of the tire near the bead portion. The fields of magnetic flux are sufficient to provide for damage detection in the bead portion without overly saturating the sensor array. The sensor device also allows for positioning the sensor array proximate to the inner surface of the tire for improved detection.

17 Claims, 10 Drawing Sheets

(51) Int. Cl.
  *G01R 33/07* (2006.01)
  *B60C 25/00* (2006.01)
  *B60C 25/05* (2006.01)
  *G01N 27/82* (2006.01)
(52) U.S. Cl.
  CPC .......... *G01R 33/072* (2013.01); *B60C 25/005* (2013.01); *B60C 25/0548* (2013.01); *G01N 27/82* (2013.01)

(56) References Cited

U.S. PATENT DOCUMENTS

| | | | |
|---|---|---|---|
| 6,550,320 B1 | 4/2003 | Giustino | |
| 6,832,513 B2 * | 12/2004 | Weiss | G01M 17/02 73/146 |
| 6,907,777 B2 * | 6/2005 | Weiss | G01M 17/02 73/146 |
| 7,506,539 B2 | 3/2009 | Miyoshi et al. | |
| 7,762,129 B2 | 7/2010 | Niklas et al. | |
| 7,826,192 B2 * | 11/2010 | Sinnett | G01M 17/022 156/123 |
| 8,051,705 B2 | 11/2011 | Kobayakawa | |
| 8,526,128 B2 | 9/2013 | Kubota et al. | |
| 8,939,020 B2 * | 1/2015 | Townsend | G01M 17/02 73/146 |
| 2002/0134910 A1 | 9/2002 | Kokubu et al. | |
| 2009/0078347 A1 | 3/2009 | Niklas | |
| 2012/0038357 A1 | 2/2012 | Brandon et al. | |
| 2013/0162265 A1 | 6/2013 | Beccavin et al. | |

OTHER PUBLICATIONS

European Search report for Application No. 14885120.7 dated Oct. 9, 2017 8 pgs.
International Search Report for PCT/US2014/026021, dated Jun. 20, 2014, 7 pages.
International Search Report for PCT/US2014/026097, dated Jun. 19, 2014, 8 pages.

* cited by examiner

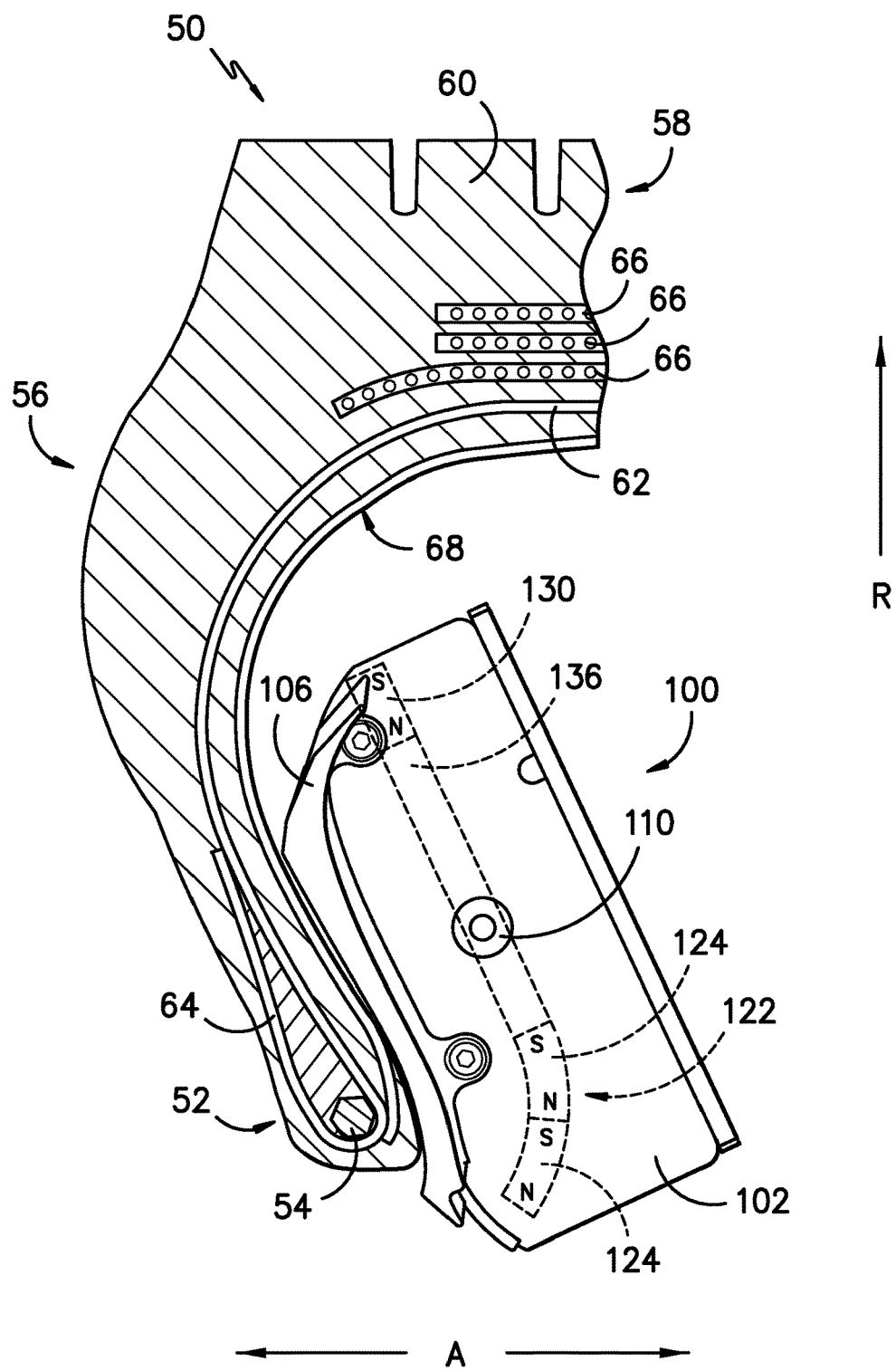
FIG. -1-

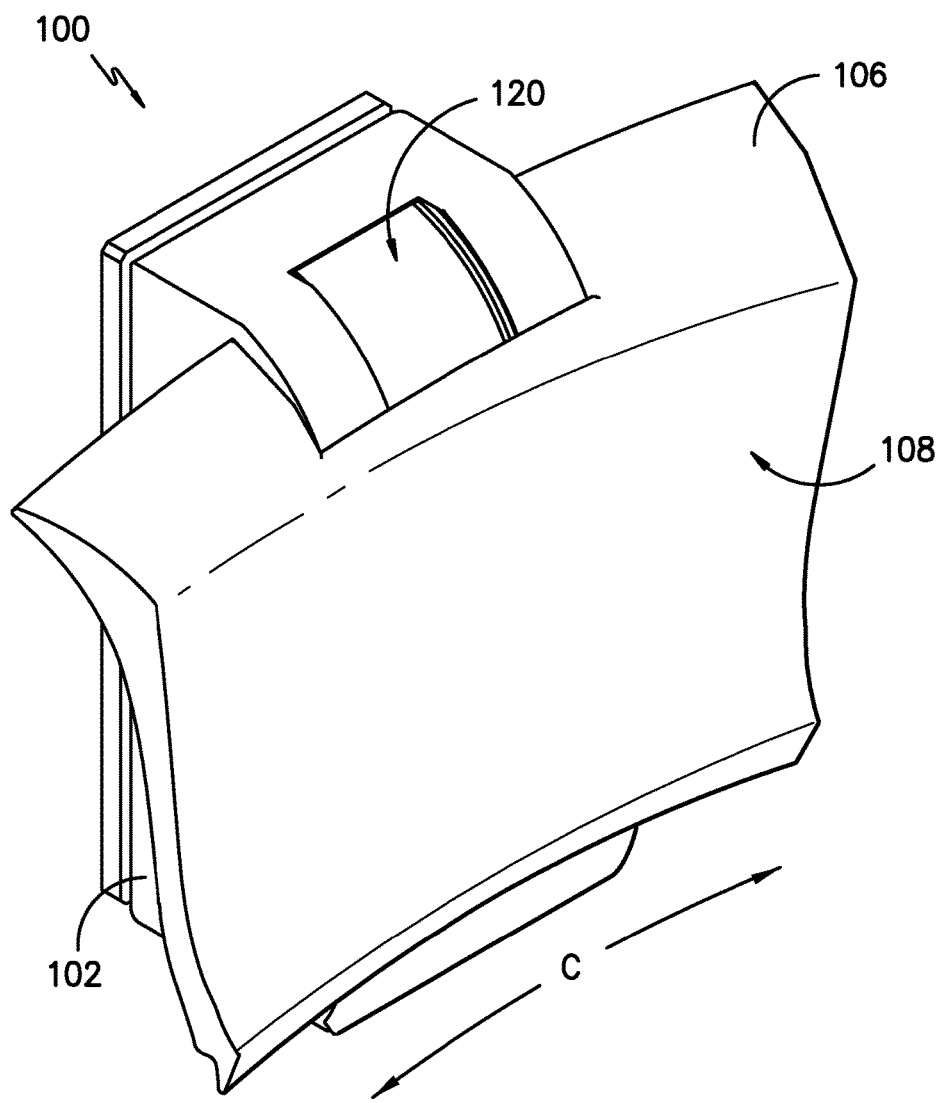
FIG. -2-

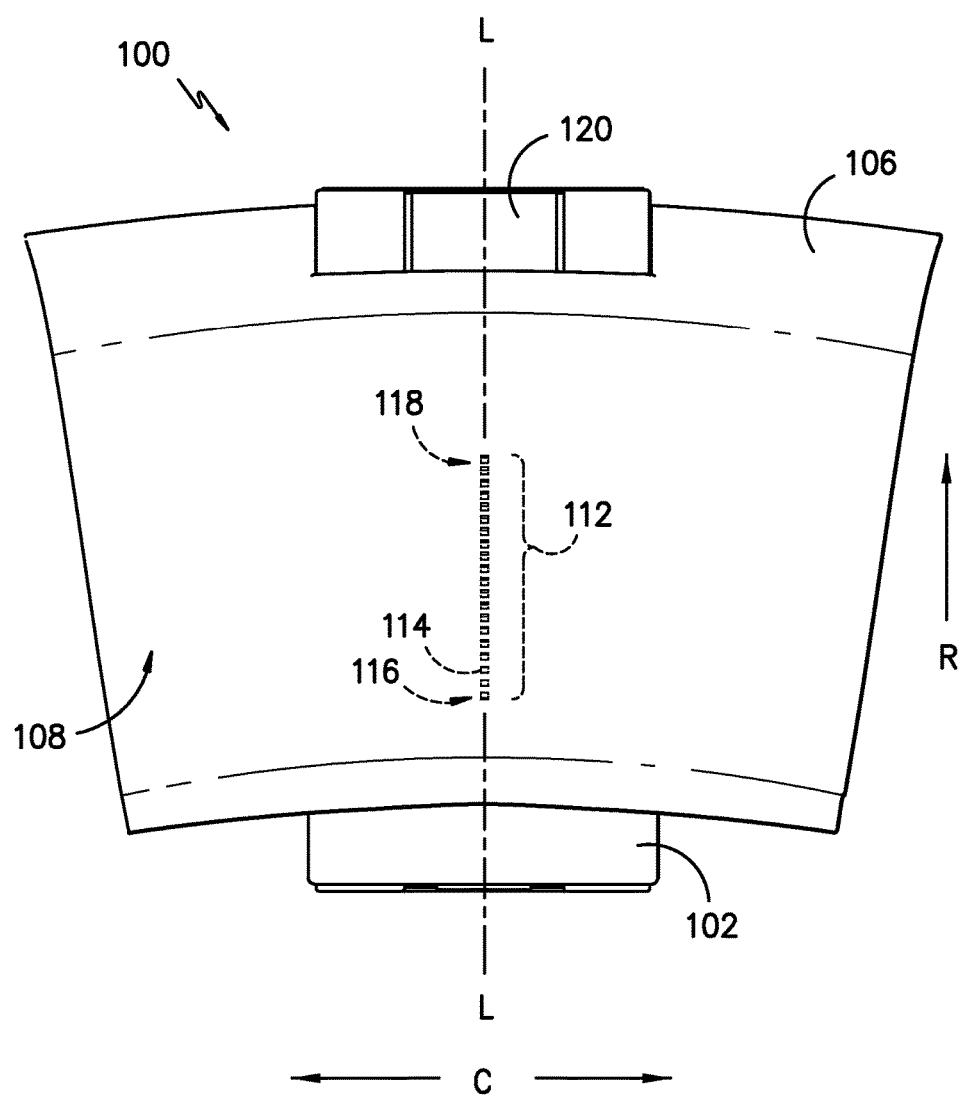
FIG. -3-

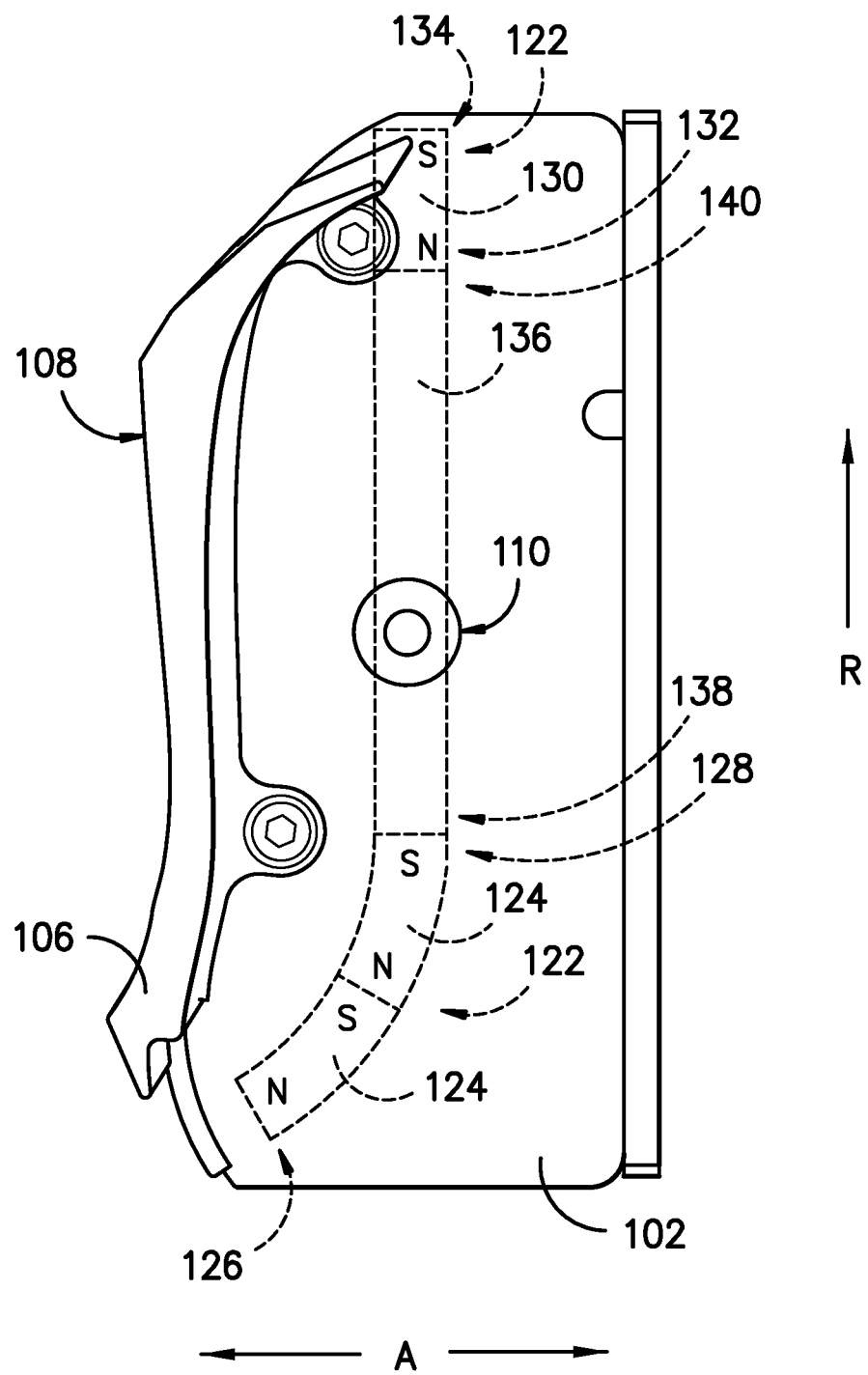
FIG. -4-

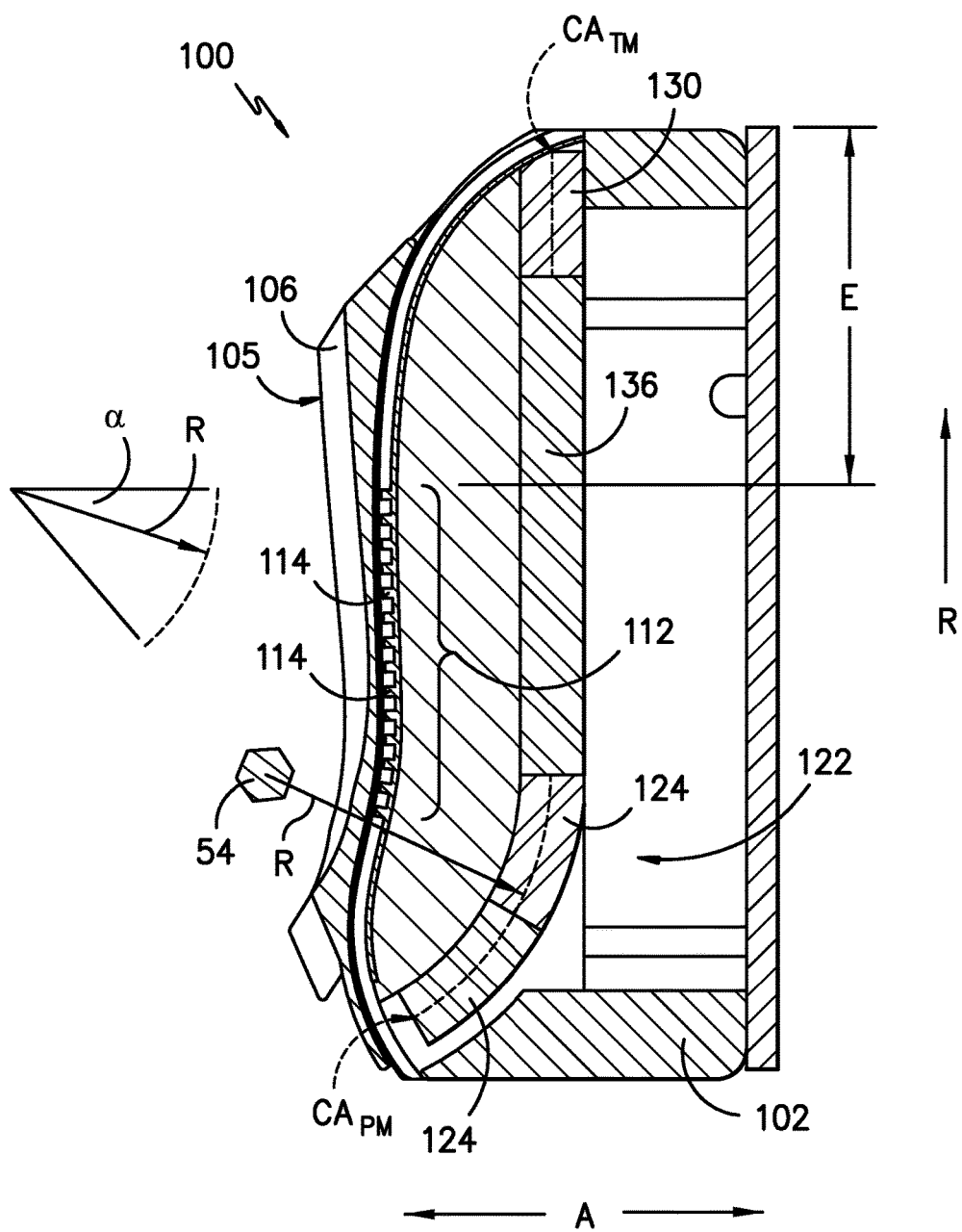
FIG. −5−

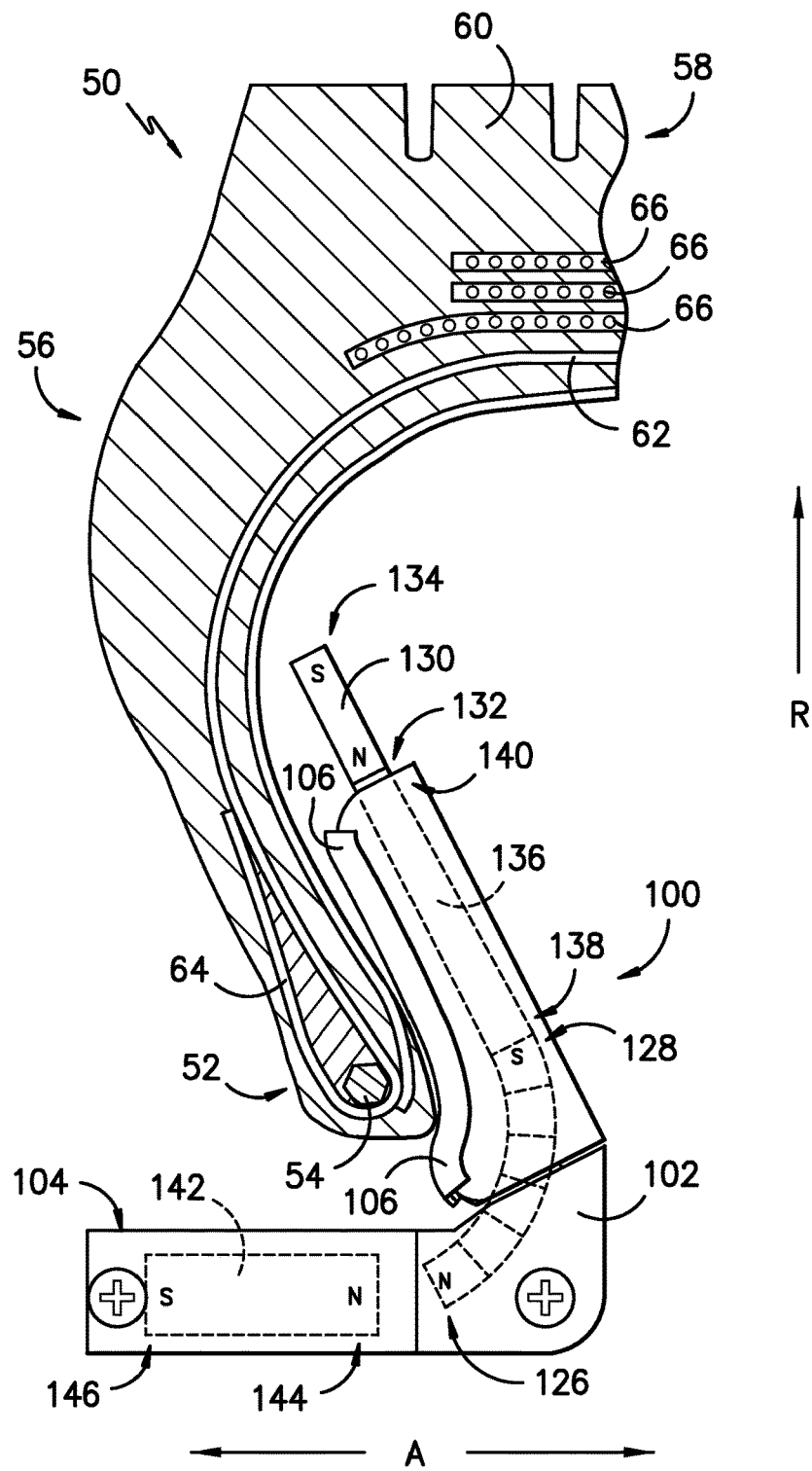
FIG. -6-

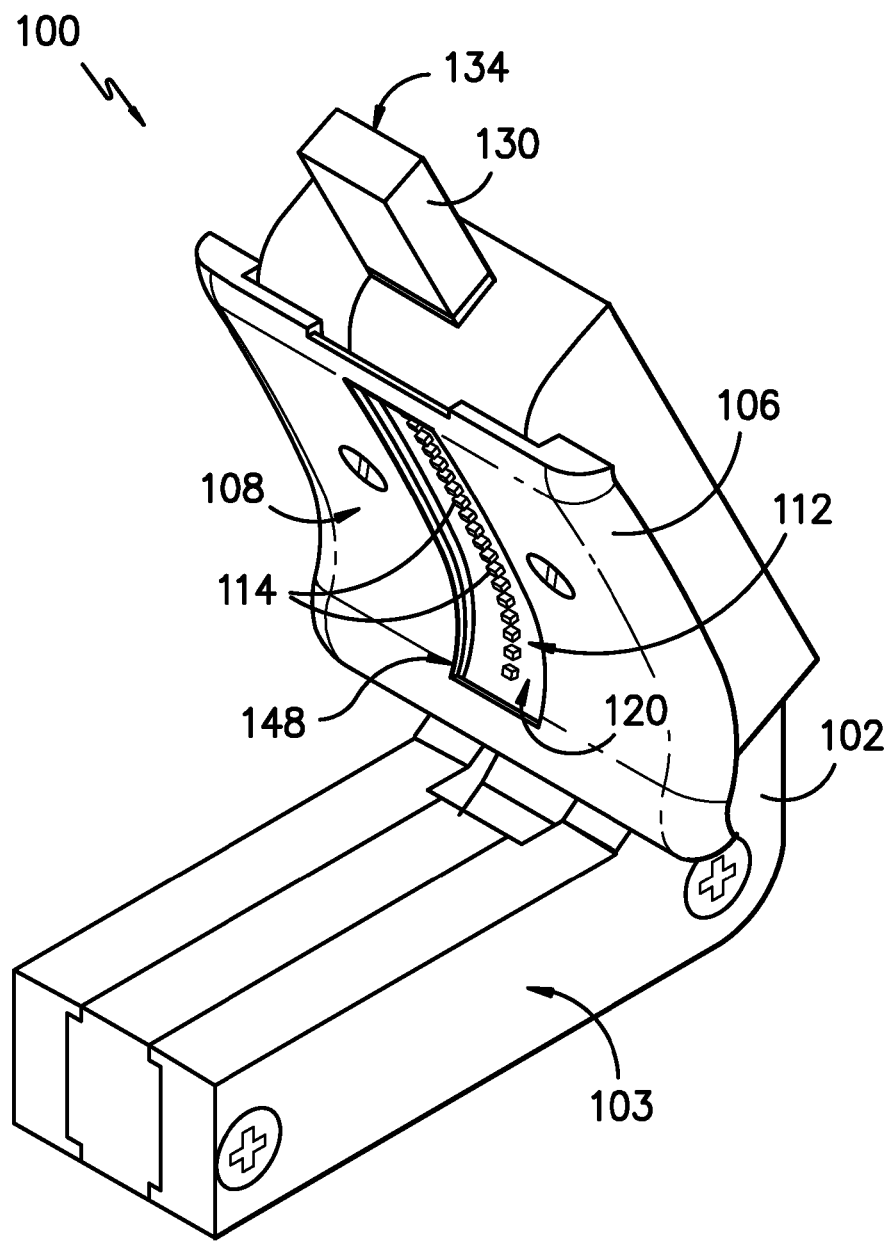
FIG. -7-

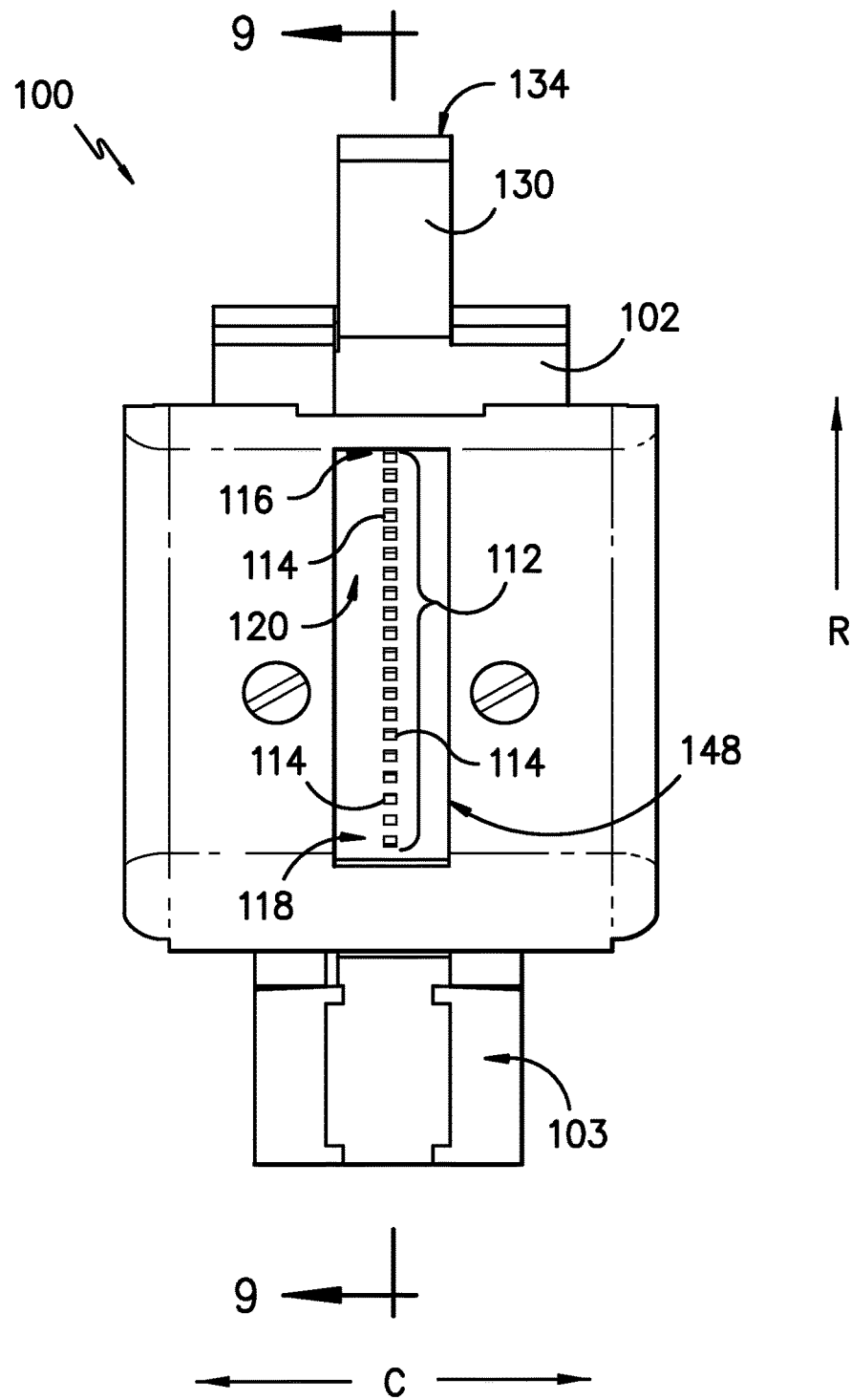
FIG. -8-

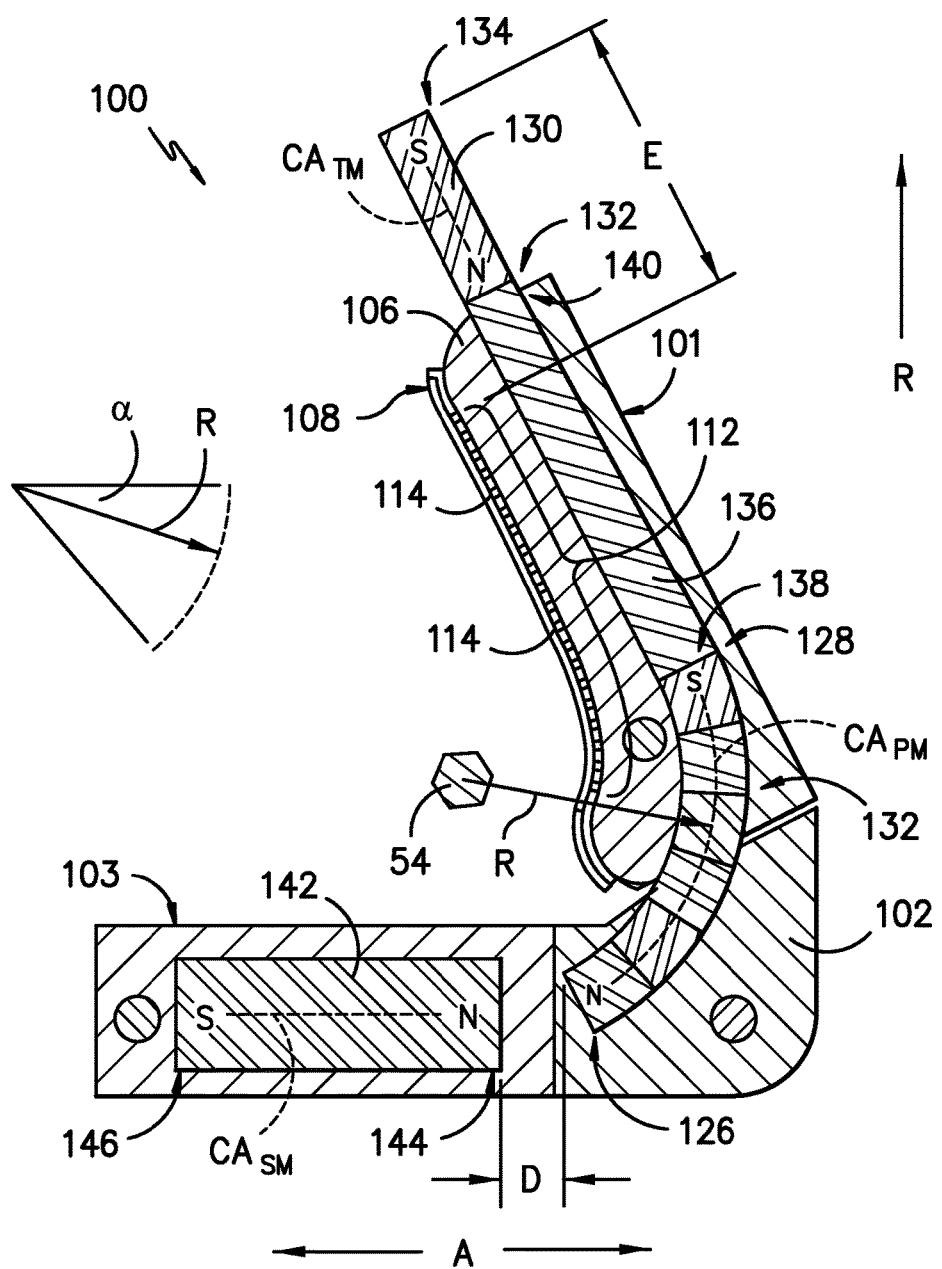
FIG. -9-

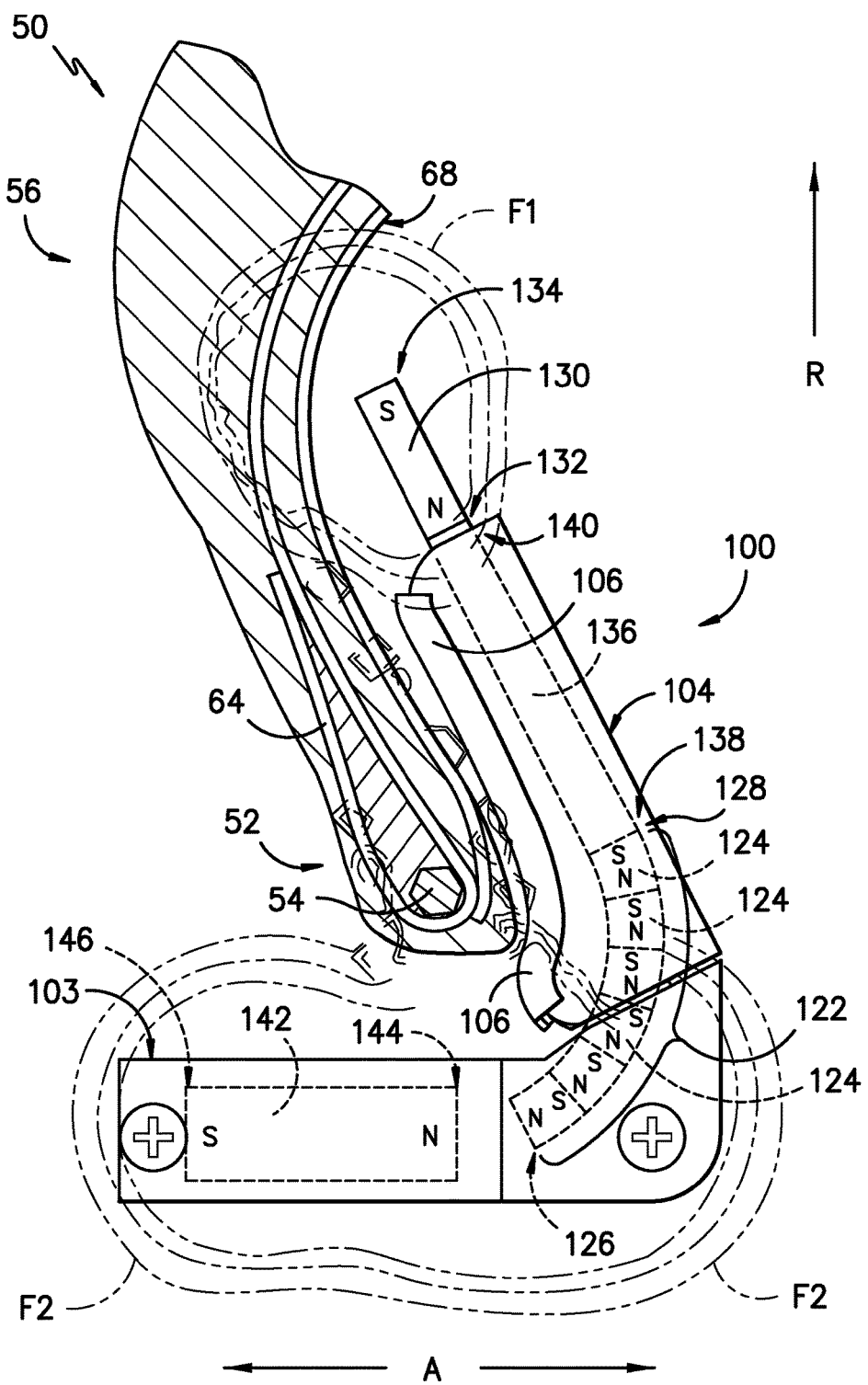
FIG. -10-

SENSOR DEVICE WITH MAGNET AND SENSOR ARRAY FOR TIRE INSPECTION

FIELD OF THE INVENTION

The subject matter of the present disclosure relates generally to a sensor device for inspecting reinforcements of a tire near the bead area.

BACKGROUND OF THE INVENTION

A known tire construction uses a body ply having reinforcement elements that extend from bead portion to bead portion through opposing sidewall portions, and a crown portion of the tire. Sometimes referred to as the carcass ply or reinforcing ply, the body ply is typically anchored at the beads and maintains the overall shape of the tire as the tire is inflated and used. The reinforcement elements of the body ply are usually oriented substantially along the radial direction (a direction perpendicular to the axis of rotation) and can include e.g., a ferrous metal.

During use of the tire, these reinforcement elements (sometimes referred to as cords) may be damaged e.g., from impact with objects in the roadway, travel over curbs, and other damaging events. In some situations, the reinforcement elements may be completely broken as a result of such an event. Unfortunately, this damage may not be readily discoverable from a visual inspection of the exterior of the tire because the reinforcement elements are contained within the rubber materials used to construct the tire.

Commercial tires are commonly reused after a process referred to as retreading. With retreading, worn tread is removed from the tire and a new tread belt or tread section is installed onto the tire. Replacement of the tread is less expensive than replacing the whole tire and allows additional mileage to be obtained using the same tire carcass. This practice is common particularly with commercial tires for heavy trucks.

Before replacing the tread, however, it is advantageous to inspect the tire, including the reinforcement elements of the body ply, for damage or wear. In certain situations, inspection may reveal that replacement of the tire is required rather than retreading. Alternatively, repair of the tire may be required. As stated above, not all damage to interior elements such as e.g., the reinforcement elements of the body ply are readily apparent from a visual inspection alone.

As the reinforcement elements for commercial tires such as heavy truck tires are frequently constructed from a ferrous material, one or more sensors can be used to detect discontinuities in the reinforcement elements such as e.g., breaks that are not otherwise ascertainable from a visual inspection of the tire. For example, magnets can be used to create fields of magnetic flux along the reinforcement elements. Sensors can be used to detect changes in the magnetic flux that are indicative of a break. It is desirable to automate such an inspection process so that multiple tires may be inspected economically and expediently. It is also desirable to minimize the amount of time required for the inspection process.

Detecting damage to the reinforcement elements of the body ply along the bead portion of the tire is problematic. Each opposing bead portion of the tire typically includes a bead that extends along the circumferential direction forming a hoop or ring. This bead is constructed of ferrous metal that can interfere with accurate detection of damage to the reinforcement elements of the body ply near the bead portion of the tire. More specifically, the bead provides a substantial amount of ferrous metal that impedes the level of saturation of the reinforcement elements with magnetic flux that is desired for break detection. Some tire constructions also use a body ply that is wrapped around the bead, which further increases the amount of ferrous metal in the area where inspection is desired. Additionally, the non-linear geometry of the bead portion also impedes efforts to place the sensors close to the surface of the tire, which is desired for improved detection sensitivity and accuracy. The non-linear geometry and presence of ferrous metal also creates problems in creating fields of magnetic flux that are properly positioned at a level sufficient for damage detection but without undesirably saturating sensors used to detect the magnetic flux.

As such, a device that can be used for tire inspection along the bead portion of the tire would be useful. More particularly, a device that can repeatedly place one or more sensors near the bead portion for detection of damage to the reinforcement elements of a body ply would be useful. Such a device that can also properly create the magnetic field desired for the damage detection would be particularly beneficial.

SUMMARY OF THE INVENTION

The present invention provides a sensor device for use in tire inspection along a bead portion of the tire. The sensor device includes a magnet array configured to provide the desired fields of magnet flux for a sensor array, which is used to detect damage to reinforcements of a body ply of the tire near the bead portion. The fields of magnetic flux are sufficient to provide for damage detection in the bead portion without overly saturating the sensor array. The sensor device also allows for positioning the sensor array proximate to the inner surface of the tire for improved detection. Additional objects and advantages of the invention will be set forth in part in the following description, or may be apparent from the description, or may be learned through practice of the invention.

In one exemplary embodiment of the present invention, a sensor device for tire inspection is provided that is removably positionable along an inner surface of a tire. The tire has a bead portion and defines a radial direction and an axial direction. The sensor device includes a body comprising an outermost inspection surface for placing at the inner surface near the bead portion. A sensor array is provided that includes a plurality of sensors arranged in a linear manner and defining a longitudinal direction. The sensor array is supported by the body and located proximate to the outermost inspection surface. The sensor array has opposing ends. A magnet array is arranged on the body so that the outer inspection surface and sensor array are located between at least a portion of the magnet array and the tire when the sensor device is positioned for tire inspection. The magnet array includes a plurality of magnets having a first end and a second end. At least a portion of the plurality of magnets are arranged into an arc of a circle and configured to partially surround the bead portion of the tire. The arc of the circle has a central angle $\alpha$, wherein 60 degrees$\leq\alpha\leq$90 degrees. The magnet also includes a terminal magnet having at least one end displaced along the longitudinal direction beyond one of the opposing ends of the sensor array.

In another exemplary embodiment, the present invention includes a sensor device for tire inspection. The tire has a bead portion and defines a radial direction and an axial direction. The sensor device includes a body having an outermost inspection surface for placing at the inner surface of the tire near the bead portion. A sensor array provides a plurality of sensors defining a longitudinal direction. The sensor array is supported by the body and is located near the outermost inspection surface. The sensor array has opposing ends. A magnet array is supported on the body. The magnet array defines a central axis along its length that is positioned within the same plane as the longitudinal direction defined by the sensor array. The magnet array includes a plurality of magnets having a first end and a second end. At least a portion of the plurality of magnets is arranged into an arc of a circle and are configured for positioning at the bead portion of the tire. The arc of the circle has a central angle α, wherein 60 degrees≤α≤90 degrees. A terminal magnet is provided having at least one end displaced along the longitudinal direction beyond one of the opposing ends of the sensor array.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 is a partial cross-sectional view of one side of a tire along with a side view of an exemplary embodiment of the present invention.

FIG. 2 illustrates a perspective view of the exemplary embodiment of the invention depicted in FIG. 1.

FIG. 3 is a front view of the exemplary embodiment of FIG. 2.

FIG. 4 is a side view of the exemplary embodiment of FIG. 2.

FIG. 5 is a cross-sectional side view of the exemplary embodiment of FIG. 2.

FIG. 6 is a partial cross-sectional view of one side of a tire along with a side view of another exemplary embodiment of the present invention.

FIG. 7 illustrates a perspective view of the exemplary embodiment of the invention depicted in FIG. 6.

FIG. 8 is a front view of the exemplary embodiment of FIG. 6.

FIG. 9 is a cross-sectional side view of the exemplary embodiment of FIG. 6.

FIG. 10 is another partial cross-sectional view of one side of a tire and a side view of the exemplary embodiment of FIG. 6 along with a depiction of a magnetic field created by this exemplary embodiment.

DETAILED DESCRIPTION

For purposes of describing the invention, reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

As used herein, the following definitions apply:

"Meridian plane" is a plane within which lies the axis of rotation of the tire. FIG. 1 is a cross-section of an exemplary tire 50 taken along a meridian plane.

The "crown portion" of the tire is the portion that extends along the axial direction A (which is the direction parallel to the axis of rotation of the tire) between the sidewall portions of the tire including the tread and components positioned radially inward of the tread.

"Body ply" or "carcass" or "carcass ply" is a ply that extends between and from the bead portions on opposing sides of the tire, through the opposing sidewall portions, and across the crown portion of the tire. The body ply may include ferrous reinforcements.

The "radial direction" is perpendicular to the axis of rotation of the tire and is denoted in the figures with an "R" and a directional arrow. The axial direction, parallel to the axis of rotation, is denoted in the figures with an "A" and directional arrows.

The "circumferential direction" of the tire (also referred to as the longitudinal direction) is the direction corresponding to the periphery of the tire and is defined by the direction of rotation of the tire during normal operation. The circumferential direction is denoted in the figures with a C and directional arrows.

In the description that follows, directions R, A, and C are denoted in drawings of the exemplary embodiments to denote their orientation relative to the tire when the sensor device is positioned for tire inspection. Additionally, the positions of various components of exemplary embodiments are described with reference to these directions as determined relative to sensor device 100 when it is positioned for tire inspection.

FIG. 1 illustrates a side view of an exemplary embodiment of sensor device 100 of the present invention in position for inspection of a representative tire 50. Only a portion of a cross-section along a meridian plane of tire 50 is shown as tire 50 is substantially symmetrical about its centerline as viewed in the meridian plane. Tire 50 includes bead portion 52 with bead 54. A body ply 62 extends from bead portion 52, through sidewall portion 56, and through crown portion 58 along both sides of tire 50. Crown portion 58 includes a tread portion 60 and belt plies 66 located radially inward of tread portion 60.

For this exemplary embodiment, sensor device 100 is removably positioned at bead portion 52 of tire 50 and adjacent to portion of its inner surface 68. Sensor device 100 may be repeatably located along the bead portion of multiple tires as may be required e.g., in a commercial facility by a positioning system (not shown) that can be connected at point of attachment 110. Sensor device 100 is useful for inspecting tire 50 particularly where it is desirable to position one or more sensors in close proximity to the inner surface 68 of tire 50 at bead portion 52 along with one or more magnets that create a field of magnetic flux for use in damage detection.

More particularly, body ply 62 includes reinforcement elements (not shown) typically constructed from a ferrous material and embedded in the rubber materials used to construct tire 50. As previously stated, reinforcement elements can be damaged during use of tire 50. During a tire inspection process, as may be part of e.g., a retreading operation, tire 50 may be inspected for damage to such reinforcement elements. For example, sensor device 100 may include one or more Hall Effect sensors as will be further described herein for detecting breaks in ferrous reinforcement elements. In other exemplary embodiments of the invention, sensor device 100 may include Hall Effect sensors, temperature sensors, optical sensors, and/or other type sensors as well.

When sensor device 100 is positioned for inspection of tire 50, sensor device 100 may be placed very close (e.g., within 5 mm to 6 mm) of inner surface 68 at bead portion 52 or may even contact inner surface 68. Once positioned, tire 50 can be rotated about its axis of rotation so as to scan or detect for broken reinforcement elements over a complete circumference of the tire. Sensor device 100 allows the placement of one or more sensors in close proximity to inner surface 52, which may be necessary for proper testing and also expedites testing by allowing a complete inspection from a single rotation of tire 50. In addition, because of the unique positioning of an array of magnets relative to the sensors, the present invention will create a field of magnetic flux that can be used to detect damage to the ferrous reinforcement elements near bead portion 52 despite the presence of a substantial amount of ferrous components at bead portion 52 including bead 54, body ply 62, and the turn-up 64 of body ply 62 that may be wrapped around bead 54 as shown in FIG. 1. At the same time, the sensors will not be oversaturated with magnetic flux, which could impede the accuracy of tire inspection.

Referring now to FIGS. 1, 2, 3, 4, and 5, sensor device 100 includes a body 102 that may be constructed from one or more parts formed integrally or attached. Body 102 includes a platform 106 that defines an outermost inspection surface 108. As used herein, "outermost" means that the inspection surface 108 is the closest part of body 102 to that portion of the inner surface 68 of tire 50 that is being inspected by the sensors. Outermost inspection surface 108 has a profile as viewed along one side (FIGS. 1 and 4) that is slightly concave (FIGS. 1 and 4) in order to facilitate its positioning adjacent to inner surface 68. Outermost inspection surface 108 is also slightly curved with respect to circumferential direction C (FIG. 3)

As shown in FIGS. 3 and 5, sensor device 100 includes a sensor array 112 located proximate to outermost inspection surface 108. For this exemplary embodiment, sensor array 112 includes a plurality of sensors 114 positioned on sensor support surface 120 located immediately beneath or behind outermost inspection surface 108. Sensors 114 are Hall Effect sensors, which detect magnetic flux and can provide a signal indicative of the presence of magnetic flux as well as the magnetic flux density. As shown in the front view of sensor device 100 provided in FIG. 3, the plurality of sensors 114 are arranged linearly and adjacent to each other. Sensors 114 also define a longitudinal direction L that is within a meridian plane of tire 50 when sensor device 100 is positioned for inspection of tire 50. Sensor array 112 also includes a first opposing end 116 separated from a second opposing end 118 along longitudinal direction L. While any number of Hall Effect sensors may be used depending upon the detection length desired for sensor array 112, in one exemplary embodiment of the invention a total of 16 Hall Effect sensors are used along longitudinal direction L for sensor array 112.

Referring now to FIGS. 1, 4, and 5, sensor device 100 also includes a magnet array 122. For this exemplary embodiment, magnet array 122 is arranged on body 102 so that the outer inspection surface 108 and sensor array 112 are closer to inner surface 68 than magnet array 122. In some embodiments, magnet array 122 is arranged on body 102 to that outer inspection surface 108 and sensor array 112 are between at least a portion of the magnet array 122 and tire 50 when sensor device 100 is positioned for tire inspection as shown in FIG. 1.

Magnet array 122 includes a plurality of magnets 124 having a first end 126 and a second end 128. (FIG. 4). The plurality of magnets 124 are arranged sequentially with alternating polarity as shown in FIG. 4. As herein, "arranged sequentially with alternating polarity" means adjacent magnets 124 are oriented with opposite poles facing each other such as e.g., N-S/N-S/N-S or S-N/S-N/S-N.

At least a portion of the plurality of magnets 124 are arranged into an arc of a circle. For this exemplary embodiment, the plurality of magnets 124 contact each along the arc and define a central axis $CA_{PM}$ (FIG. 5). Central axis $CA_{PM}$ lies in the same plane (a meridian plane of tire 50) as the longitudinal direction L defined by sensor array 112 in this embodiment. The arc of the circle has a radius R and a central angle $\alpha$. When sensor device 100 is positioned for tire inspection, radius R originates in bead 54 and sweeps over central angle $\alpha$, which is in the range of 60 degrees to 90 degrees, or 60 degrees$\leq\alpha\leq$90 degrees. This arrangement of at least a portion of the plurality of magnets 124 into the arc of a circle ensures that such magnets 124 at least partially surround bead portion 52. For the exemplary embodiment shown in FIGS. 1 through 5, central angle $\alpha$ is about 60 degrees.

Continuing with FIGS. 4 and 5, magnet array 122 also includes a terminal magnet 130 having a first end 132, a second end 134, and also defining a central axis $CA_{TM}$. As shown, first end 132 is located radially inward of second end 134. Second end 134 is displaced along longitudinal direction L by a predetermined distance E from the second end 118 of sensor array 112. More particularly, predetermined distance E represents the distance between second end 134 of terminal magnet 130 and the second opposing end 118 of sensor array 112. This displacement of second end 134 ensures that the plurality of sensors 114 of sensor array 112 are not overly saturated with magnetic flux, which could interfere with proper detection of damage to that portion of the reinforcements in body ply 62 located adjacent to outermost inspection surface 108 during tire inspection. In one exemplary embodiment, predetermined distance E is about 10 mm to about 15 mm. In another exemplary embodiment, predetermined distance E is about 13 mm. The polarity of terminal magnet 130 is also arranged sequentially with alternating polarity relative to the plurality of magnets 124.

Continuing with FIGS. 4 and 5, sensor device 100 includes a connecting bar 136 having a first end 138 and a second end 140. Connecting bar 136 may be constructed from ferrous metal such as steel and is used to help distribute magnetic flux created by the plurality of magnets 124 and the terminal magnet 130. Connecting bar 136 extends between second end 128 of the plurality of magnets 124 and first end 132 of terminal magnet 130. In one exemplary embodiment, connecting bar 136 has a cross-sectional area (in a plane perpendicular to the meridian plane of tire 50) at first end 138 that is substantially equal to the cross-sectional area of the second end 128 of plurality of magnets 124. Similarly, connecting bar 136 has a cross-sectional area at second end 138 that is substantially equal to the cross-sectional area of the first end 132 of terminal magnet 130.

In an alternative embodiment of the present invention, connecting bar 136 is replaced by extending the plurality of magnets 124. More particularly, for this alternative embodiment, the plurality of magnets 124 can be extended linearly along longitudinal direction L and into contact with (or proximate to) first end 132 of terminal magnet 130. The extension of the plurality of magnets 124 could be accomplished with multiple magnets arranged sequentially with alternating polarity or by a single magnet having a length comparable to connecting bar 134. Regardless, such magnets or magnet would be arranged sequentially with alternating polarity between the magnets 124 in the arc of the circle and terminal magnet 130. In addition, although shown as a single magnet, terminal magnet 130 could be a plurality of magnets arranged sequentially with alternating polarity provided that second end 134 is displaced by predetermined distance E as already described.

FIGS. 6, 7, 8, 9, and 10 illustrate another exemplary embodiment of a sensor device 100 of the present invention, wherein the use of the same reference numerals denotes the same or similar features as already described for the exemplary embodiment of FIGS. 1, 2, 3, 4, 5, and 6. For the exemplary embodiment of FIGS. 6, 7, 8, 9, and 10, sensor device 100 includes a sensor body 102 having a first arm portion 101 and a second arm portion 103 that form an acute angle with respect to one another. First arm portion 101 supports sensor array 112 and magnet array 122. In addition, for this exemplary embodiment, magnet array 122 includes a supplemental magnet 142 supported by second arm portion 103. Supplemental magnet 142 has a central axis $CA_{SM}$ (FIG. 9) extending along axial direction A. For this exemplary embodiment, central axis $CA_{SM}$ lines within the same plane as central axis $CA_{PM}$ and central axis $CA_{TM}$. It should be understood that in other exemplary embodiments, the three central axes $CA_{SM}$, $CA_{PM}$ and central axis $CA_{TM}$ may not line in the same plane.

As shown, supplemental magnet 142 has a first end 144 separated longitudinally along $CA_{SM}$ by a second end 146. First end 144 of supplemental magnet 142 and first end of plurality of magnets 124 are positioned radially inward of bead portion 52 when sensor device 100 is in position for tire inspection (FIG. 10). In addition, the first end 144 of supplemental magnet 142 has a polarity that is the same as the polarity of the first end 126 of plurality of magnets 124. For this exemplary embodiment, first end 126 and first end 144 are separated by a predetermined distance D (FIG. 9). In one embodiment, predetermined distance D is in the range of 5 mm to 15 mm. In another embodiment, predetermined distance D is about 10 mm. Although shown as a single magnet, supplemental magnet 142 could be a plurality of magnets arranged sequentially with alternating polarity provided that first end 144 is displaced by predetermined distance D as already described.

The exemplary embodiment of 6, 7, 8, 9, and 10 also includes an aperture 148 in outermost inspection surface 108 that surrounds sensor array 112. Sensor support surface 120 is slightly recessed relative to outmost inspection surface 108 so as to protect sensor array 112 during tire inspection. Other configurations may be used as well.

FIG. 10 provides an exemplary of the use of sensor device 100 for inspection of tire 50. More particularly, FIG. 10 shows representative fields F1 and F2 of magnetic flux created by magnet array 122. As shown, field F1 is created along a shoulder region of sidewall 56 while field F2 is created around bead portion 52. Importantly, the magnetic flux does not overly saturate sensor array 112, which would preclude accurate detection of breaks in the reinforcements of body ply 62 in the region of interest. At the same time, enough magnetic flux is provided for detection despite the presence of substantial ferrous material in bead portion 52.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A sensor device for tire inspection that is removably positionable along an inner surface of a tire, the tire having a bead portion and defining a radial direction and an axial direction, the sensor device comprising:
a body comprising an outermost inspection surface for placing at the inner surface near the bead portion;
a sensor array comprising a plurality of sensors arranged in a linear manner and defining a longitudinal direction, the sensor array supported by the body and located proximate to the outermost inspection surface, the sensor array having opposing ends;
a magnet array arranged on the body so that the outer inspection surface and sensor array are located between at least a portion of the magnet array and the tire when the sensor device is positioned for tire inspection, the magnet array comprising
a plurality of magnets having a first end and a second end, wherein at least a portion of the plurality of magnets are arranged into an arc of a circle and configured to partially surround the bead portion of the tire, the arc of the circle having a central angle α, wherein 60 degrees≤α≤90 degrees; and
a terminal magnet having at least one end displaced along the longitudinal direction beyond one of the opposing ends of the sensor array.

2. The sensor device of claim 1, wherein the magnet array further comprises a supplemental magnet supported by the body and having a first end and a second end, wherein the supplemental magnet and the first end of the plurality of magnets are located radially inward of the bead portion when the sensor device is positioned for inspection of the tire, and wherein the first end of the supplement magnet and the first end of the plurality of magnets are of the same polarity.

3. The sensor device of claim 2, wherein the first end of the plurality of magnets and the first end of the supplemental magnet are separated from each other by a predetermined distance.

4. The sensor device of claim 3, wherein the predetermined distance separating the first ends of the supplemental magnet and the plurality of magnets is in the range of 5 mm to 15 mm.

5. The sensor device of claim 4, wherein the predetermined distance separating the first ends of the supplemental magnet and the plurality of magnets is about 10 mm.

6. The sensor device of claim 1, wherein the plurality of magnets are arranged sequentially with alternating polarity.

7. The sensor device of claim 6, wherein the plurality of magnets contact each other along the arc of the circle.

8. The sensor device of claim 1, further comprising a connecting bar extending between the second end of the plurality of magnets and the terminal magnet, the connecting bar comprising a ferrous metal.

9. The sensor device of claim 8, wherein the connecting bar has a cross-sectional area along an end that is substantially equal to a cross-sectional area of the second end of the plurality of magnets and an end of the terminal magnet.

10. The sensor device of claim 1, wherein the second end of the plurality of magnets is positioned adjacent to the terminal magnet and arranged sequentially in alternating polarity with the terminal magnet.

11. The sensor device of claim 1, wherein the outermost inspection surface defines an aperture surrounding the sensor array.

12. The sensor device of claim 1, wherein the sensor array comprises a plurality of Hall Effect sensors.

13. The sensor device of claim 1, wherein the plurality of magnets defines a central axis that lies in the same plane as the plurality of sensors of the sensor array.

14. The sensor device of claim 1, wherein the arc of the circle is defined by a radius with a center that is located in the bead portion of the tire when the sensor device is positioned for tire inspection.

15. A sensor device for tire inspection, the tire having a bead portion and defining a radial direction and an axial direction, the sensor device comprising:
   a body comprising an outermost inspection surface for placing at the inner surface of the tire near the bead portion;
   a sensor array comprising a plurality of sensors defining a longitudinal direction, the sensor array supported by the body and located near the outermost inspection surface, the sensor array having opposing ends;
   a magnet array supported on the body, the magnet array defining a central axis along its length that is positioned within the same plane as the longitudinal direction defined by the sensor array, the magnet array comprising
   a plurality of magnets having a first end and a second end, wherein at least a portion of the plurality of magnets are arranged into an arc of a circle and configured for positioning at the bead portion of the tire, the arc of the circle having a central angle α, wherein 60 degrees≤α≤90 degrees; and
   a terminal magnet having at least one end displaced along the longitudinal direction beyond one of the opposing ends of the sensor array.

16. The sensor device for tire inspection as in claim 15, further comprising a supplemental magnet supported by the body and having a first end and a second end, wherein the supplemental magnet and the first end of the plurality of magnets are located radially inward of the bead portion when the sensor device is positioned for inspection of the tire, and wherein the first end of the supplement magnet and the first end of the plurality of magnets are of the same polarity.

17. The sensor device for tire inspection as in claim 16, wherein the body further comprises:
   a first arm portion on which the sensor array is positioned; and
   a second arm portion on which the supplemental magnet is positioned;
   wherein the first arm portion and second arm portion form an angle into which the bead portion of the tire is positioned during tire inspection.

* * * * *